United States Patent [19]

Naegeli

[11] Patent Number: 4,877,904
[45] Date of Patent: Oct. 31, 1989

[54] BICYCLIC KETONES AS ODORANTS AND FLAVORANTS

[75] Inventor: Peter Naegeli, Wettingen, Switzerland

[73] Assignee: Givaudan Corporation, Clifton, N.J.

[21] Appl. No.: 94,560

[22] Filed: Sep. 9, 1987

[30] Foreign Application Priority Data

Sep. 18, 1986 [CH] Switzerland .................. 3740/86

[51] Int. Cl.[4] ............................................. C07C 49/21
[52] U.S. Cl. ...................................... 568/374; 512/21;
426/538; 568/345; 568/353
[58] Field of Search ....................................... 568/374

[56] References Cited

U.S. PATENT DOCUMENTS

| | | | |
|---|---|---|---|
| 3,256,333 | 6/1966 | Doubenko | 568/374 |
| 3,703,479 | 11/1972 | Theimer | 568/374 |
| 3,773,836 | 11/1973 | Hall | 568/374 |
| 3,816,350 | 6/1974 | Hall | 568/374 |
| 3,989,739 | 11/1976 | Stadler et al. | 568/374 |
| 4,617,146 | 10/1986 | Helmlinger et al. | 568/374 |

FOREIGN PATENT DOCUMENTS 2440406 3/1976 Fed. Rep. of Germany ...... 568/374

OTHER PUBLICATIONS

Klumpp et al., Tetrahedron Letters, vol. 24, pp. 4595–8 (1983).
T. E. Bellas et al., Tetrahedron 30, (1974) 2267–2271.
Chem. Abstract 93: 72025e [for H. Iwamuro et al.; 23rd Proceedings of the Chem. Soc. Jap. (1979) 86–7].

Primary Examiner—James H. Reamer
Attorney, Agent, or Firm—Robert F. Travares; Linda A. Vag

[57] ABSTRACT

Novel odorant and/or flavoring substances are described. These are the compounds of the formula

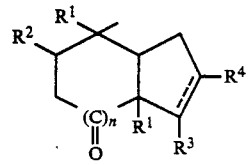

wherein:
$R^1$ represents methyl or ethyl,
$R^2$ represents hydrogen or methyl,
the dotted line represents an optional carbon-carbon bond,
n is 0 or 1, and,
when n is O, $R^3$ is hydrogen and $R^4$ represents acetyl or propronyl, and,
when n is 1, $R^3$ represents methyl or ethyl and $R^4$ represents hydrogen or methyl,
with the exception of 1,4,4,7a-tetramethyl-3a,4,5,7a-tetrahydro-7(6H)-ind-1-enone.

The compounds of formula I possess organoleptic properties which make them particularly suitable for use as odorant and/or flavoring substances.

8 Claims, No Drawings

BICYCLIC KETONES AS ODORANTS AND FLAVORANTS

THE INVENTION

The present invention concerns novel odorants and flavorants of the formula

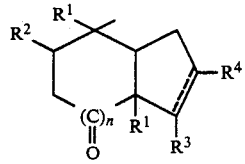

wherein:
- $R^1$ represents methyl or ethyl,
- $R^2$ represents hydrogen or methyl,
- the dotted line represents an optional carbon-carbon bond,
- n is 0 or 1, and,
- when n is 0, $R^3$ is hydrogen and $R^4$ represents acetyl or propionyl, and,
- when n is 1, $R^3$ represents methyl or ethyl and $R^4$ represents hydrogen or methyl, with the exception of 1,4,4,7a-tetramethyl-3a,4,5,7a-tetrahydro-7(6H)-ind-1-enone, namely the compound of the formula

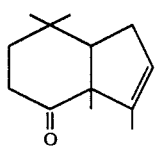

Compounds of formula I possess various asymmetric carbon atoms and may therefore exist as mixtures of stereoisomers. Formula I is intended to embrace all possible stereoisomers which result from the various asymmetric centers.

The compounds of formula I possess organoleptic properties which make them particularly suitable for use as odorant and/or flavoring substances. The invention, therefore, also concerns odorant and/or flavoring substance compositions containing compounds of formula I and methods for making same.

The invention also concerns a process for the manufacture of compounds of formula I. This process comprises cyclizing either a compound of formula II

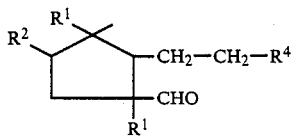

wherein $R^1$ and $R^2$ have the above significance and $R^4$ signifies acetyl or propionyl, or a compound of formula III

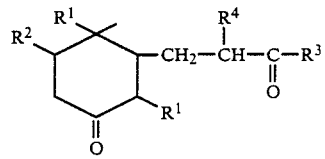

wherein $R^1$ and $R^2$ have the above significance, $R^3$ represents methyl or ethyl and $R^4$ represents hydrogen or methyl, and, if desired, hydrogenating the carbon-carbon double bond present in the reaction product obtained.

DESCRIPTION OF THE PREFERRED EMBODIMENTS

The cyclization of a compound of formula II may be effected by means of bases such as alkali metal or alkaline earth metal hydroxides or carbonates. The cyclization is conveniently carried out in a solvent such as a hydrocarbon, an alcohol or an ether and at room temperature or, preferably, at an elevated temperature.

The cyclization of a compound of formula III may be effected by means of protonic acids such as mineral acids (hydrochloric acid, sulphuric acid, phosphoric acid, perchloric acid, etc.) or by means of organic sulphonic acids such as p-toluenesulphonic acid. The suitable reaction conditions are analogous.

The compounds of formula I obtained in the cyclization of either a compound of formula II or III may be hydrogenated to remove the carbon-carbon double bond if desired. The hydrogenation may be effected catalytically. Noble metal catalysts on suitable carriers are preferred e.g., Pd/C. The presence of a solvent is optional; suitable solvents are alcohols, esters and hydrocarbons.

The compounds of formulas II and III are preferably prepared in situ, either from compounds of the formula

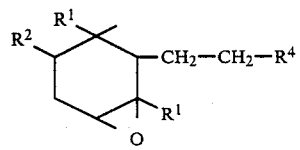

under the influence of Lewis acids, or from compounds of the formula

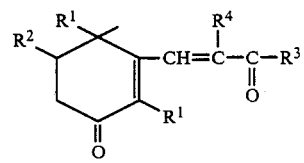

by means of catalytic hydrogenation. Lewis acids that are suitable for the conversion of compounds of formula IV are, for example, $SnCl_4$, $TiCl_4$ and the like, preferably $BF_3$ (etherate). Suitable solvents are ethers and (chlorinated) aliphatics and aromatics, preferably methylene chloride. The reaction conditions are preferably mild, e.g. a temperature range of about $-20°$ C. to about $+50°$ C. is convenient.

Suitable catalysts for the hydrogenation of a compound of formula V are palladium and platinum, with or without a carrier. Pd/C is preferred. It is preferred to conduct the hydrogenation in the presence of a base and in aliphatic solvents, or in alcohols, etc.

The compounds of formula I, which are used in accordance with the invention as odorant and/or flavoring substances, are distinguished by agreeable, pronounced natural eucalyptus notes. They are powerful and fresh-camphorous-borneol like, without having the volatility of the eucalyptus oil top notes. The side notes which appear are: (slightly) fruity, tobacco-like, cedar-like, spicy, patchouli-like and pine-like. Moreover, they are distinguished by a high diffusion capacity, combined with an extraordinary fixation. Even when used in low concentrations they intensify and enrich the olfactory character of odorant substance compositions, especially of fougère-like, chypre-like, woody, animal compositions or bases. The compounds of formula I combine with numerous known odorant substance ingredients of natural or synthetic origin, whereby the range of the natural raw materials can embrace not only readily-volatile, but also moderately-volatile and difficulty-volatile components and that of the synthetics can embrace representatives from practically all classes of substances, as is evident from the following compilation:

Natural products: Basil oil, tree moss absolute, mugwort oil, bergamot oil, cassis bud absolute, castoreum, cedarwood oil, ciste labdanum, civet, coriander oil, oak moss, elemi oil, pine needle oil, galbanum, geranium oil, clove oil, jasmin absolute and its synthetic substitute, jonquille absolute, camomile oil, labdanum, lavender oil, mandarin oil, mastix absolute, mentha citrata oil, myrrh oil, palmarosa oil, patchouli oil, petitgrain oil Paraguay, sandalwood oil, thyme oil, vassoura oil, musk infusion, styrax, birch tar, vetiver oil, frankincense, ylang-ylang oil, lemon oil, civet oil, etc.

Alcohols: Citronellol, Dimetol ® (Givaudan) (2,6-dimethyl-heptan-2-ol), geraniol, cis-3-hexenol, linalool, 6,8-dimethyl-nonan-2-ol, phenylethyl alcohol, rhodinol, Sandela ® (Givaudan) (Lb 3-isocamphyl-5-cyclohexanol), Sandalore ® (Givaudan) (3-methyl-5-(2',2',3'-trimethyl-cyclopenta-3'-en-1'-yl)-pentan-2-ol), terpineol, etc.

Aldehydes: α-Amylcinnamaldehyde, cyclamen aldehyde, decanal, dodecanal, heliotropin, α-hexylcinnamaldehyde, hydroxycitronellal, lyral, Adoxal TM (Givaudan) (2,6,10-trimethyl-9-en-1-al), undecanal, ω-undecylene aldehyde, vanillin, etc.

Ketones: Isoradleine ® (Givaudan) (isomethyl-α-ionone), α-ionone, β-ionone, 3-prenylisocaranone, acetylated cedarwood oil, p-methylacetophenone, etc.

Esters: Ethyl acetonacetate, amyl salicylate, benzyl acetate, cedryl acetate, cinnamyl formate, citronellyl acetate, geranyl aetate, cis-3-hexenyl acetate, cis-3-hexenyl benzoate, linalyl acetate, linalyl anthranilate, methyl dihydrojasmonate, 1-acetoxy-1-methyl-2-sec.-butylcyclohexane, 4-(4-methyl-3-pentenyl)cyclohex-3-en-1-yl-carbinyl acetate, phenoxyethyl isobutyrate, phenylethyl tiglate, styrallyl acetate, terpenyl acetate, 2,3,6,6-tetramethylcyclohex-2-ene-carboxylic acid ethyl ester, 3,6,6-trimethyl-2-ethyl-cyclohex-2-ene-carboxylic acid ethyl ester, vetivenyl acetate, ortho-tert-butylcyclohexyl acetate, etc.

Various: Musk ambrette, coumarin, epoxycedrene, eugenol, Fixolide ® (Givaudan) (1,1,2,4,4,7-hexamethyl-6-acetyl-1,2,3,4-tetrahydronaphthalene), Galaxolid ® (IFF) (1,3,4,6,7,8-hexahydro-4,6,6,7,8,8-hexamethylcyclopenta-γ-2-benzopyran), heliotropin, indole, indolene, isoeugenol, isobutylquinoline, jasmonyl (1,3-diacetoxy-nonane), musk ketone, limonene, p-methane-8-thiol-3-one, 1-methylcyclododecyl methyl ether, methyl-eugenol, 12-oxahexadecanolide, γ-nonalactone, γ-undecalactone, etc.

The compounds of formula I (or mixtures thereof) can be used in compositions in wide limits which can range, for example, from 0.1% (detergents) to 30% (alcoholic solutions). It will, however, be appreciated that these values are not limiting values, as the experienced perfumer can also achieve effects with even lower concentrations or can synthesis novel complexes with even higher dosages. The preferred concentrations range between 0.1 and 25%. The compositions manufactured with I can be used for all kinds of perfumed consumer goods (eau de cologne, eau de toilette, extracts, lotions, creams, shampoos, soaps, salves, powders, toothpastes, mouth washes, deodorants, detergents, tobacco, etc.).

The compounds of formula I (or mixtures thereof) can accordingly be used in the manufacture of compositions and, as will be evident from the above compilation, a wide range of known odorant substances or odorant substance mixtures can be used. In the manufacture of such compositions the known odorant substances or odorant substance mixtures mentioned above can be used according to methods known the perfumer, such as e.g. according W. A. Poucher, Perfumes, Cosmetics, Soaps 2, 7th Edition, Chapman and Hall, London 1974.

The novel compounds of formula I are also excellently suited for use in flavors of the widest variety of kind, but especially also for the flavoring of tobacco.

As flavoring substances the compounds of formula I can be used, for example, for the production or improvement, intensification, enhancement or modification of fruit flavors, e.g. blueberry or blackberry flavors. As fields of use for these flavors there come into consideration, for example, foodstuffs (yoghurt, confectionery etc.), semi-luxury consumables (tea, tobacco etc) and drinks (lemonade etc).

The pronounced flavor qualities of the compounds of formula I enable them to be used as flavouring substances in low concentrations. A suitable dosage embraces, for example, the range of 0.01 ppm–100 ppm, preferably the range of 0.01 ppm–20 ppm, in the finished product, i.e. the flavored foodstuff, semi-luxury consumable or drink.

In the flavoring of, for example, tobacco the dosage can, however, also lie higher and can embrace a wider range, for example the range of 1 to 1000 ppm, preferably 30–100 ppm.

The compounds can be mixed with the ingredients used for flavoring compositions or added to such flavorants in the usual manner. Under the flavorants used in accordance with the invention there are to be understood flavoring compositions which can be diluted or distributed in edible materials in a manner known per se. They contain, for example, about 0.1–10, especially 0.5–3, wt.%. They can be converted according to methods known per se into the usual forms of use such as solutions, pastes or powders. The products can be spray-dried, vacuum-dried or lyophilized.

The known flavoring substances which are conveniently used in the manufacture of such flavorants are either already referred to in the above compilation or can be taken readily from the literature such as e.g. J. Merory, Food Flavorings, Composition, Manufacture and Use, Second Edition, The Avi Publishing Company, Inc., Westport, Conn. 1968, or G. Fenaroli, Fenaroli's Handbook of Flavor Ingredients, Second Edition, Volume 2, CRC Press, Inc, Cleveland, Ohio, 1975.

For the manufacture of such usual forms of use there come into consideration, for example, the following carrier materials, thickening agents, flavor improvers, spices and auxilliary ingredients, etc:

Gum arabic, tragacanth, salts or brewers' yeast, alginates, carrageen or similar absorbents; indoles, maltol, dienals, spice oleoresins, smoke flavors; cloves, diacetyl, sodium citrate; monosodium glutamate, disodium inosine-5'-monophosphate (IMP), disodium guanosine-5-phosphate (GMP); or special flavoring substances, water, ethanol, propylene glycol, glycerine, etc.

ILLUSTRATION OF THE PREFERRED EMBODIMENTS

A number of examples are provided herein to illustrate the preferred embodiments of this invention. The examples are included for the sole purpose of illustration and should not be construed as limiting. They are intended to embrace any equivalents or obvious extensions which are known or should be known to a person skilled in the art.

EXAMPLE 1

(a) 60 g of 3-(3-oxobutyl)-2,4,4-trimethyl-cyclohexanone (product of the catalytic hydrogenation of 4-ketoionone with palladium-carbon in ethyl acetate at room temperature and normal pressure, see H. Jwamuro et al., 23rd Proceedings of the Chemical Society of Japan, 86 [1979]) are dissolved in 500 ml of diethyl ether and at the reflux temperature of the solution there are immediately added dropwise while stirring 25 ml of 80% sulphuric acid. A further 25 ml of 80% sulphuric acid are added dropwise four times after a reaction time of 1 hour in each case. 30 minutes after the last addition of the brownish reaction mmixture is poured onto ice, diluted with water to about 1.5 l, the emulsion is broken with ammonium sulphate and the aqueous phase is separated. After washing with sodium bicarbonate solution and water the organic phase is dried as usual and evaporated under a vacuum. After flat distillation at 55°–60° C./0.05 Torr there are obtained 46 g of 1,4,4,7a-tetramethyl-3a,4,5,7a-tetrahydro-7(6H)-ind-1-enone.

Odor: reminiscent of dried fruits, camphor-like/cineol-like, but clinging, woody/terpene-like, reminiscent of honey, slightly patchouli-like.

MS: m/e=192(40), 177(35), 159(5), 149(6), 135(32), 123(28), 121(27), 107(27), 99(31), 95(100), 79(55).

IR (film): 1700, 1470, 1445, 1375, 1235, 1150, 1080, 1025, 835 cm$^{-1}$.

NMR (400 MHz in CDCl$_3$): $\delta$=4.47 ppm (1H, narrow m); $\delta$=2.125 ppm (1H, dxdd, J=2/7/8 Hz), $\delta$=1.99 ppm (1H, dxdd, J=7/9/14 Hz); $\delta$=1.55 ppm (3H, narrow m); $\delta$=1.25 ppm (3H, s); $\delta$=1.00 ppm (3H, s); $\delta$=0.924 ppm (3H, s).

(b) Alternative variant: the educt is dissolved in a 6 to 7 fold amount by weight of glacial acetic acid, 1/5–1/7 of the volume of 70% perchloric acid is added thereto in the cold and the solution is left to stir at room temperature for 4 hours. The working-up is effected analogously to that above.

(c) The cyclization reaction of the diketone can finally be carried out analogously with the acid of p-toluene-sulphonic acid in boiling toluene solution.

EXAMPLE 2

1.92 g of the above bicyclic ketone I are dissolved in 200 ml of hexane and hydrogenated under a hydrogen atmosphere at room temperature with 1 g of 5% palladium on carbon as the catalyst. After filtration over Celite the mixture is evaporated and the product is flat distilled.

B.p. of the 1,4,4,7a-tetramethyl-3a,4,5,7a-tetrahydro-7(6H)-indanone: ~80° C./0.03 Torr.

Odor: fresh, powerful, good fixation, slightly woody.

MS: m/e=194(10), 179(40), 161(7), 152(18), 139(100), 123(58), 109(46), 95(72), 81(45).

IR (film): 1695, 1460–1480, 1375–1380, 1250, 1140, 1120, 1040, 920 cm$^{-1}$.

NMR (400 MHz, CDCl$_3$): Main isomer exhibits $\delta$=2.455 ppm (1H, dxt, J=9/19 Hz); $\delta$=2.15 ppm (1H, dxdd, J=19/9/3 Hz); 1.235 ppm (3H, s); $\delta$=0.98 ppm (3H, s); $\delta$=0.92 ppm (3H, s); $\delta$=0.90 ppm (3H, d, J=7 Hz).

EXAMPLE 3

The preferred process for the manufacture of the compounds I (n=1) is exemplified on the basis of two typical representatives, with the educts which are subjected to the cyclization being obtained from the known, doubly unsaturated diketones. Their processing can be effected without isolation and/or purification.

A. 1-Ethyl-4,4,7a-trimethyl-3a,4,5,7a-tetrahydro-7(6H)-ind-1-enone:

95 g of 2,4,4-trimethyl-3-(3-oxo-1-pentenyl)-2-cyclohexen-1-one are dissolved in 1.5 l of hydrogenation alcohol, 34 g of potassium hydroxide pellets are added thereto and finally 10 g of 5% palladium-carbon are added. Thereupon, the mixture is stirred intensively under a hydrogen atmosphere until the uptake of gas has ended (about 15 hours). After filtration from the catalyst over Celite the solution is concentrated in a vacuum, diluted with water and extracted with hexane. After drying and removal of the solvent there remain behind 90 g of a viscous oil which crystallizes slowly. Analysis of the product indicates that, in addition to the saturated monocyclic diketone III, a larger amount of bridged bicyclic aldol is formed. This fact has no influence on the subsequent cyclization reaction, as this aldol opens again under the cyclization conditions to III and reacts in the desired direction to I. The above crude product III is thereupon dissolved in 445 ml of glacial acetic acid and 89 ml of 70% perchloric acid in the cold, stirred at room temperature for 5 hours, then poured on to ice/water (in excess) and exhaustively extracted with hexane. After washing neutral and drying as well as evaporation of the organic solvent the crude product I is fractionally distilled in a packed column after it has been freed from the high-boiling residues by flat distillation on a short Vigreux column at 83°–102° C./0.05 Torr.

B. 1,2,4,4,7a-Pentamethyl-3a,4,5,7a-tetrahydro-7(6H)-ind-1-enone:

The 2-(2-methyl-3-oxobut-1-enyl)-1,3,3-trimethylcyclohexene used as the starting material is obtained by isomerizing 3-(2-methyl-3-oxobut-1-enyl)-2,4,4-trimethylcyclohexene with a 1:1 mixture of conc. sulphuric acid and ether or dichloromethane at room temperature within 16 hours. It is washed neutral with water, dried and flat distilled under a vacuum. 123 g of this product are added dropwise under reflux temperature to a solution of 99 g of N-hydroxyphthalimide in 2.1 l of acetone, thereupon 1.7 g of dibenzoyl peroxide are added and the solution is left to react for 24 hours with the aid of a gasification stirrer in an oxygen stream of 150 ml/min. The reaction mixture is immediately evaporated and the residue is taken up at 50° C. in 1.2 l of tetrachloromethane, thereupon rotated at 15° C. in a rotary evaporator in order to improve crystallization and the crystal slurry is filtered (rinsing of the filter cake with CCl₄). The filtrate is immediately treated while cooling with a solution of 200 ml of pyridine and 70 ml of acetic anhydride, whereby the occurrence of heating is inhibited. The solution is stirred at room temperature for 12 hours and then evaporated. The 179 g of crude product V are filtered in a hexane-ether solution (4:1) over 270 g of neutral aluminium oxide (activity II). The evaporated eluate is treated with 60 g of paraffin oil and distilled at 0.06 Torr/125° C. Where the subsequent catalytic hydrogenation of the product with 10% palladium-carbon does not proceed spontaneously, the distillate must again be taken up in ether, triturated with 10% ferrous sulphate solution and again distilled after the usual working-up. The yield of 3-(2-methyl-3-oxobut-1-enyl)-2,4,4-trimethyl-cyclohex-2-enone amounts to 63%.

MS: m/e=220(23), 205(5), 191(9), 177(50), 164(23), 149(16), 136(30), 123(10), 107(10), 91(12), 77(20).

IR (film): 1670, 1600, 1365, 1350, 1330, 1300, 1250, 1200, 1150, 1100, 1030, 995, 885 cm⁻¹.

NMR (400 MHz, CDCl₃). $\delta=7.1$ ppm (1H, narrow m); $\delta=2.55$ ppm (2H, dd, J=6/7 Hz); $\delta=2.415$ ppm (3H, s); $\delta=1.925$ ppm (2H, broad t, J=7/6 Hz); $\delta=1.69$ and 1.625 ppm (in each case narrowest d, J=1 Hz); $\delta=1.18$ ppm (6H, s).

UV (EtOH): $\lambda_{max}=258$ nm ($\epsilon=11600$).

77 g of the above intermediate are dissolved in 150 ml of absolute alcohol, the precipitate is filtered off and the filtrate is diluted with 1.7 l of absolute alcohol. 35 g of 85% potassium hydroxide and 14.8 g of 10% prehydrogenated palladium on carbon are added thereto and the mixture is stirred under a hydrogen atmosphere until the hydrogen uptake has ended. After filtration under a protective gas the solution is concentrated, the product is taken up in water and exhaustively extracted with hexane. After washing neutral the organic phase is dried and evaporated. From the 65 g of oily crude product III there can be obtained from the solution in a small amount of hexane by cooling about 15 g of the bicyclic fused aldol (m.p. about 84° C). For the manufacture of the compound I, the crude product III of the hydrogenation can be dissolved directly in 150 ml of glacial acetic acid plus 30 ml of 70% perchloric acid. After stirring at room temperature (16 hours) the mixture is exhaustively extracted with hexane, washed neutral with water and sodium bicarbonate, dried and evaporated. The oily crude product (~45 g) is short-path distilled or fractionally distilled and gives 26 g of pure product I.

Physical date of the thus-prepared products III (n=1) and I (n=1):

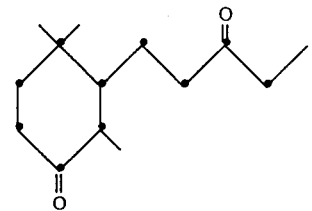

See Example 3B.
B.p.: 120° C./0.05 Torr.
MS: m/e=224(1), 206(2), 195(4), 191(2), 177(6), 168(5), 163(2), 152(100), 139(50), 125(28), 111(50), 97(25), 81(18), 69(39), 57(98), 43(84).

IR (film): 1710, 1470, 1460, 1415, 1390, 1370, 1350, 1155, 1115, 1010 cm⁻¹.

NMR (400 MHz, CDCl₃).
Main isomer: $\delta=1.07$ ppm (3H, s); $\delta=1.06$ ppm (3H, t, J=7 Hz); $\delta=1.05$ ppm (3H, d, J=6 Hz); $\delta=0.99$ ppm (3H, s).

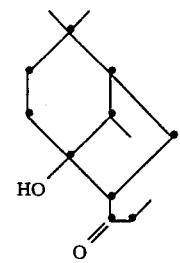

"bridged bicyclic aldol"

See Example 3A.
MS m/e: 224(8), 206(3), 195(10), 177(4), 168(3), 153(51), 139(100), 125(21), 107(9), 97(27), 84(69), 69(26), 57(82), 43(40).

IR (CDCl₃): 3550, 1700, 1475, 1460, 1390, 1380, 1370, 1350, 1180, 1140, 1080, 950, 9210 cm⁻¹.

NMR (400 MHz, CDCl₃): $\delta=2.99$ ppm (1H, dd, J=12/6 Hz); $\delta=2.73$ ppm (1H, dq, J=18/7 Hz); $\delta=2.46$ pp, (1H, dq; J=18/7 Hz); $\delta=2.18$ ppm (1H, dd, J=14/6 Hz); $\delta=2.05$ ppm (1H, q, J=7 Hz); $\delta=1.43$ ppm (1H, dxdd, J=13/6 Hz); $\delta=1.38$ ppm (1H, br.d, J=7 Hz); $\delta=1.1$ ppm (1H, dxm, J=14 Hz); $\delta=1.055$ ppm (3H, t, J=7 Hz); $\delta=1.01$ ppm (34H, d, J=7 Hz); $\delta=0.965$ and 0.90 ppm (in each case 3H, s).

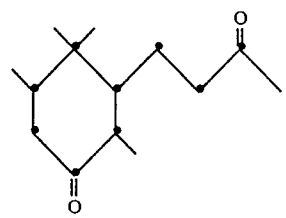

Analogous to Example 3A.
Main isomer:
MS m/e: 224,209,191, (all traces), 166(25), 153/154(5-6), 137/139(2-3), 123(7), 111(22-25), 97(9-12), 83(15), 69(30-35), 55(33), 43(100).

IR (film): 1710, 1460, 1425, 1380-1360, 1285, 1190, 1170, 1080, 1040, 995 cm⁻¹.

NMR (400 MHz, CDCl₃): δ=2.15 ppm (3H, s); δ=2.10 ppm (1H, dxdd, J=14/4/2 Hz); δ=1.96 ppm (1H, m); δ=1.08 ppm (3H, d, J=7 Hz); δ=1.01 ppm (3H, s); δ=0.965 ppm (3H, d, J=6 Hz); δ=0.92 ppm (3H, s).

Secondary isomer: m.p. 40° C.
MS: as above.
IR (KBr): 1700, 1470, 1455, 1430, 1410, 1400, 1375/1360, 1340, 1275, 1245, 1230, 1175, 1170, 1050, 970, 995, 925, 890, 805 cm⁻¹.

NMR (400 MHz, CDCl₃): δ=2.545 ppm (1H, dxdd, J=17/11/5 Hz); δ=2.42 ppm (1H, dxdd, J=17/11/5 Hz); δ=2.145 ppm (3H, s); δ=1.91 ppm (1H, m); δ=1.645 ppm (1H, m); δ=1.585 ppm (3H, s); δ=1.465 ppm (1H, m); δ=1.05 ppm (3H, d, J=6 Hz); δ=0.995 ppm (1H, dxdd); δ=0.965 ppm (3H, s); δ=0.94 ppm (3H, d, J=6 Hz); δ=0.90 ppm (3H, s).

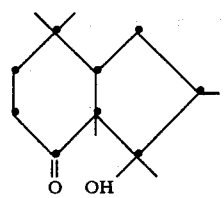

"fused bicyclic aldol"

See Example 3B.
MS: m/e=224(1), 209(1), 206(8), 191(4), 179(1), 168(3), 163(5), 152(100), 149(13), 139(20), 125(49), 109(19), 93(12), 81(8), 72(18), 69(20), 55(28), 43(86).
IR (CDCl₃): 3600, 3530, 1680, 1460, 1380, 1155, 1012, 925, 890 cm⁻¹.
NMR (400 MHz, CDCl₃): δ=1.22 ppm (3H, s); δ=1.12 ppm (3H, s); δ=0.965 ppm (3H, s); δ=0.94 ppm (3H, d, J=6 Hz); δ=0.84 ppm (3H, s).

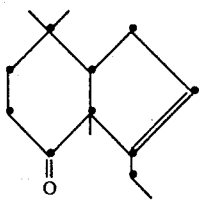

See Example 3A.
B.p. 90° C./=0.02 Torr.
Odor: very powerful, camphor-like, woody, cedar-like, reminiscent of irone, patchouli, eucalyptus, tobacco-like, long-lasting.
MS: m/e=206(31), 191(12), 177(43), 163(13), 149(40), 135(20), 121(29), 109(100), 99(24), 93(97), 81(66), 69/67(31-33), 55(40), 43(73).
IR (film): 1700, 1460, 1420, 1390, 1370, 1315, 1270, 1235, 1190, 1140, 1120, 1090, 1060, 1030, 1010, 885, 830 cm⁻¹.
NMR (440 MHz, CDCl₃): δ=5.48 ppm (1H, q, narrow); δ=2.265 ppm (1H, dxdd, J=17/9/7 Hz); δ=2.125 ppm (1H, dxdd, J=10/6/2 Hz); δ=1.995 ppm (1H, dxdd, J=17/9/7); δ=1.245 ppm (3H, s); δ=1.01 ppm (3H, t, J=7 Hz); δ=0.995 ppm (3H, s); δ=0.93 ppm (3H, s).

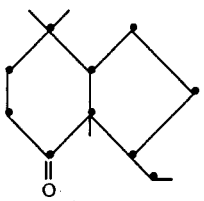

Analogous to Example 2.
B.p. 60° C./0.02 Torr.
Odor: fresh, after cineol, camphor-like, sweet, strong and homogeneous, woody.
MS: m/e=208(14), 193(31), 179(12), 165(10), 152(50), 139(100), 123(31), 109(62), 97(37), 81(35), 69(24), 55(39), 43(45), 28(45).
IR (film): 1692, 1460, 1410, 1385, 1370, 1240, 1130, 1110, 1025, 1000, 945, 925, 885 cm⁻¹.
NMR (400 MHz, CDCl₃): Isomer A: δ=1.25 ppm (3H, s); δ=0.97 ppm (3H, s); δ=0.92 ppm (3H, s); δ=0.85 ppm (3H, t, J=Hz). Isomer B: δ=0.99 ppm (3H, s); δ=0.925 ppm (3H, s); δ=0.875 ppm (3H, t, J=7 Hz); δ=0.83 ppm (3H, s).

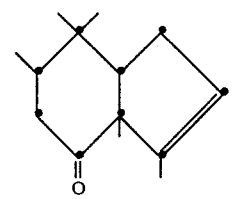

Analogous to Example 3A.
Odor: strong, clinging, ionone-like, camphor like, woody.
MS: m/e=206(23), 191(28), 177/173(2), 163(4), 149(2), 135(47), 95(100), 91(23), 79(56), 69(27), 55(26), 41(53).
IR (film): 3040, 1700, 1450, 1412, 1392, 1370, 1320, 1285, 1235, 1190, 1092, 1030, 945, 830/810/792 cm⁻¹.
NMR (400 MHz), CDCl₃): δ=5.335 ppm (1H, m narrow); δ=2.43 ppm (1H, dd, J=18/6 Hz); δ=2.255 ppm (1H, broad d, J=17 Hz); δ=2.07 ppm (1H, dd, J=8.5/3 Hz); δ=2.04 ppm (1H, dd, J=17/12 Hz); δ=1.92 ppm (1H, pseudo septet); δ=1.71 ppm (3H, narrow m); δ=1.225 ppm (3H, s); δ=0.925 ppm (3H, d, J=7 Hz); δ=0.92 ppm (3H, s); δ=0.655 ppm (3H, s).

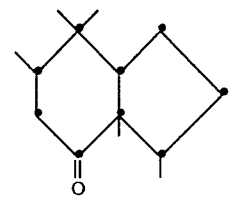

Analogous to Example 2.
B.p.: 76° C./0.02 Torr.
Odor: camphor like, sugary, woody/cedar-like.
MS: m/e=208(13), 193(100), 190(6), 175(10), 166(28), 153(62), 138(45), 123(93), 109(90), 95(75), 81(50), 69(70), 55(55), 41(64).
IR (film): 1700, 1450, 1410, 1390, 1372, 1320, 1270, 1250, 1210, 1130, 1105, 1032, 945, 864 cm⁻¹.

NMR (400 MHz, CDCl₃): 2 isomers about 50/50: $\delta = 1.215$ and 1.035 ppm (in each case 3H, s); $\delta = 0.995$ and 0.94 ppm (in each case 3H, d, J = 6.5 Hz and 7 Hz); $\delta = 0.905$ and 0.90 ppm (in each case 3H, d, J = 6.5 Hz and 7 Hz); $\delta = 0.935$ and 0.895 ppm (in each case 3H, s); $\delta = 0.635$ and 0.58 ppm (in each case 3H, s).

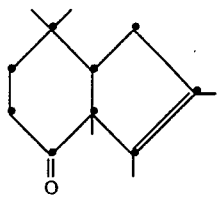

See Example 3B.
B.p. 89° C./0.08 Torr.
Odor: camphor-like, minty, after fir needles, woody, slightly fruity-flowery.
MS m/e: 206(46), 191(12), 198(2), 163(20), 149(100), 135(25), 121(24), 108(80), 93(69), 81(20), 77(24), 71(29), 55(25), 43(75).
IR (film): 1700, 1620, 1470, 1445, 1390, 1370, 1240, 1155, 1128, 1086, 1030/1020, 900, 870 cm⁻¹.
NMR (400 MHz, CDCl₃): $\delta = 1.64$ ppm (3H, narrowest d, J = 1 Hz); $\delta = 1.48$ ppm (1H, finely split m); $\delta = 1.415$ ppm (3H, narrow m); $\delta = 1.21$ ppm (3H, s); $\delta = 0.98$ ppm (3H, s); $\delta = 0.92$ ppm (3H, s).

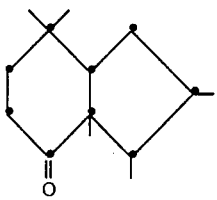

Analogous to Example 2.
B.p. 90° C./0.1 Torr.
Odor: camphor-like, homogeneous, earthy, after terpentine, reminiscent of fir resin, woody.
MS: m/e = 208(10), 193(30), 177(4), 175(5), 165(1), 152(33), 139(100), 137(31), 123(30), 109(60), 97(44), 83(37), 69(43), 55(64), 41(69).
IR (film): 1695, 1460, 1410, 1390/1380/1370, 1320, 1255, 1240, 1185, 1130, 1110, 1030, 890 cm⁻¹.
NMR (400 MHz, CDCl₃): $\delta = 2.41$ ppm (1H, dxdd, J = 20/10/8 Hz); $\delta = 1.93$ ppm (1H, dxdd, J = 14/10/8 Hz); $\delta = 1.26$ ppm (3H, s); $\delta = 0.94$ ppm (3H, d, J = 6.5 Hz); $\delta = 0.93$ ppm (3H, s); $\delta = 0.87$ ppm (3H, s); $\delta = 0.75$ ppm (3H, d, J = 7 Hz).

EXAMPLE 4

5 ml of boron trifluoride etherate are added dropwise while stirring intensively at −25° C. in 1–2 minutes to a solution of 50 g of dihydro-α-ionone epoxide in 1.5 l of methylene chloride. The reaction vessel is then cooled by means of an ice-bath. The reaction mixture attains 0° C. in about 15 minutes. Thereupon, the mixture is stirred for 5 minutes with 150 ml of 2N soda solution, the organic phase is separated and the aqueous phase is back-extracted twice. The combined methylene chloride extracts are washed neutral, dried and evaporated at 50° C. in a water-jet vacuum. The top fraction (6.5 g) comprising the volatile byproducts is separated from the crude product at 50°–68° C./0.035 Torr. The main product 11 (41 g) distils at 70°–78° C./0.035 Torr. Analysis shows a content of 80% of 1-formyl-1,3,3-trimethyl-2-(3-oxobutyl)-cyclopentane:

MS: m/e = 195(3), 192(5), 177(5), 167(14), 163(5), 154(17), 152(8), 149(15), 135(8), 123(36), 109(46), 95(38), 81(24), 69(30), 58(18), 55(29), 43(100).

IR (film): 2710, 1720, 1460, 1368, 1245, 1160, 950 cm⁻¹.

NMR (400 MHz, CDCl₃): $\delta = 9.70$ ppm (1H, s): $\delta = 2.12$ ppm (3H, s); $\delta = 1.175$ ppm (3H, s); $\delta = 1.055$ ppm (3H, s): $\delta = 0.89$ ppm (3H, s).

This material is cyclized without additional purification. For this purpose, the 41 g of product are heated to reflux temperature in 410 ml of methanolic potassium hydroxide solution (1N KOH in 90% MeOH) for 50 minutes, cooled, diluted with 3.5 l of water and exhaustively extracted with hexane. After the usual washing neutral, drying and evaporation of the organic phase in a water-jet vacuum the oily crude product is fractionally distilled. After the top fractions (4 g) the pure 1 (n=0), i.e. 3-acetyl-1,6,6-trimethyl-bicyclo[3.3.0]-oct-2-ene, (22 g) passes over at 65° C./0.05 Torr.

UV (EtOH): $\lambda_{max} = 240$ nm ($\epsilon = 11800$).

Odor: camphor-like, fruity, woody, direction of p-tert-butyl-cyclohexyl acetate.

MS: m/e = 192(5), 177(5), 159(3), 149(7), 136(7), 123(30), 107(15), 95(30), 79(9), 69(10), 55(10), 43(100).

IR (film): 1668, 1625/1612, 1455, 1372, 1362, 1305, 1265, 1230, 1170, 1042, 995, 985, 950, 868 cm⁻¹.

NMR (400 MHz, CDCl₃): $\delta = 6.39$ ppm (1H, narrow t, J = 1 Hz); $\delta = 2.29$ ppm (3H, s); $\delta = 1.86$ ppm (1H, dd, J = 8/4 Hz); $\delta = 1.235$ ppm (3H, s); $\delta = 1.00$ ppm (3H, s); $\delta = 0.85$ ppm (3H, s).

EXAMPLE 5

3.8 g of unsaturated compound 1 (n=0) of Example 4 are dissolved in 50 ml of ethanol, 500 mg of KOH (85% pellets) and then 500 mg of 5% palladium-carbon are added thereto and the mixture is stirred intensively under a hydrogen atmosphere for 12 hours. The solution is then concentrated, diluted with hexane/water, from the catalyst is filtered off and the organic phase is washed neutral, dried and evaporated. The resulting 3.5 g of hydrogenated compound 1 are short-path distilled under the vacuum of an oil pump. The pure product, 3-acetyl-1,6,6-trimethyl-bicyclo[3.3.0]-octane, (2.9 g) exhibits a camphor-like, flowery, ionone-like woody odor.

MS: m/e = 194(7), 179(10), 176(6), 161(9), 151(8), 136(5), 125(38), 109(60), 95(80), 81(68), 69/68/67(23/20/21), 55(25), 43(100).

IR (film): 1712, 1460, 1385/1370/1360, 1275, 1218, 1168, 1120/1110, 1085, 1040, 1000, 960/947, 925, 910, 872, 850, 812 cm⁻¹.

NMR (400 MHz, CDCl₃): main isomer $\delta = 2.75$ ppm (1H, dq J = 18/6 Hz); $\delta = 2.14$ ppm (3H, s); $\delta = 1.15$ ppm (3H, s); $\delta = 0.955$ ppm (3H, s); $\delta = 0.93$ ppm (3H, s).

The following compounds are manufactured analogously to Example 4 and 5:

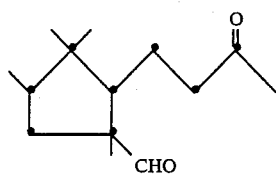

MS: m/e=224(<1), 206(1), 196(1), 191(<1), 181(8), 167(5), 154(8), 137(13), 123(12), 109(11), 96(8), 95(10), 81(13), 69(19), 58(6), 55(13), 43(100).

IR (film): 2715, 1720, 1460, 1415, 1370, 1270, 1225, 1170, 1100, 1075/1060, 1025, 975, 950, 912, 870/855 cm⁻¹.

NMR (400 MHz, CDCl₃): δ=9.69 ppm (1H, s); δ=2.485 ppm (2H, m); δ=2.23 ppm (1H, dd, J=13/7 Hz); δ=2.13 ppm (3H, s); δ=1.84 ppm (1H, sextet, J=7 Hz); δ=1.205 ppm (3H, s); δ=1.17 ppm (1H, dd, J=13/7 Hz); δ=0.94 ppm (3H, d, J=7 Hz); δ=0.91 ppm and 0.915 ppm (in each case 3H, s).

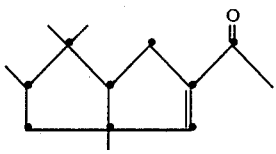

B.p.: 75° C./0.05 Torr.
Odor: fruity, tobacco-like, rosy, woody, fresh, after eucalyptus.

UV (EtOH): λ$_{max}$=240 nm (ε=12250).

MS: m/e=224(trace), 206(10), 191(7), 173(3), 163(10), 149(5), 135(15), 123(83), 107(25), 91(12), 77(11), 69(14), 55(16), 43(100).

IR (film) 1670, 1630, 1455, 1380, 1365, 1300, 1280, 1260, 1245, 1220, 1165, 1045, 1022, 960, 872 cm⁻¹.

NMR (400 MHz, CDCl₃): δ=6.32 ppm (1H, t, J=2 Hz); δ=2.62 ppm (1H, ddxdd, J=17/9/2 Hz) and δ=2.53 ppm (1H, ddxdd, J=17/4.5/2 Hz); δ=2.285 ppm (3H, s); δ=2.00 ppm (1H, dd, J=9/4.5 Hz); δ=1.745 ppm (1H, dd, J=13.6 Hz); δ=1.56 ppm (1H, pseudo septet); δ=1.38 ppm (1H, dd, J=12/11 Hz); δ=1.27 ppm (3H, s); δ=0.89 ppm (3H, s); δ=0.845 ppm (3H, s); δ=0.815 ppm (3H, d, J=6.5 Hz).

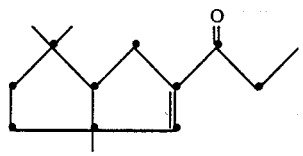

UV (EtOH): λ$_{max}$=240 nm (ε=11200).
B.p.: 80° C./0.07 Torr.
Odor: camphor-like, hot, woody, spicy, vetiver-like, after pine needles, green, eucalyptus-like.

MS: m/e=206(24), 191(6), 177(100), 159(13), 149(30), 137(28), 121(140), 107(49), 93(32), 79/77(24), 69(29), 57(100), 41(25), 29(49).

IR (film): 1670, 1640/1615, 1460, 1415, 1375, 1365, 1300, 1250, 1225, 1210/1200, 1160, 1082, 1062, 1010/995/985, 930, 895, 875, 835, 800, 700 cm⁻¹.

NMR (400 MHz, CDCl₃): δ=6.38 ppm (1H, t, J=2 Hz); δ=2.66 ppm (2H, q, J=7 Hz); δ=2.56 and 2.505 ppm (in each case 1H, ddxdd); δ=1.85 ppm (1H, dd, J=8/3.5 Hz); δ=1.675 ppm (2H, m); δ=1.395 ppm (2H, m); δ=1.225 ppm (3H, s); δ=1.095 ppm (3H, t, J=7 Hz); δ=1.00 ppm (3H, s); δ=0.85 ppm (3H, s).

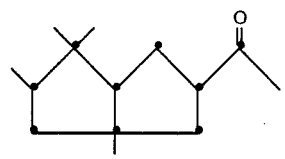

B.p.: 90° C./0.08 Torr (isomer mixture).
Odor: camphor-like, woody, tobacco-like, patchouli-like, animal-like.

MS; m/e=208(18), 193(12), 175(34), 165(5), 151(4), 135(25), 123(83), 109(37), 95(29), 81(100), 69(45), 55(34), 43(95).

IR (film): 1710, 1460, 1385/1375/1362, 1275, 1255/1245, 1235, 1215, 1165, 1100, 1045, 950 cm⁻¹.

NMR (400 MHz, CDCl₃): δ=2.835 ppm and δ=2.725 ppm and δ=2.695 ppm (together 1H, q, J=7 and 6 and 5 Hz); δ=2.145 and 2.135 ppm (together 3H, s); δ=1.13 and 1.115 ppm (together 3H, s); δ=0.805 ppm (3H, d, J=6 Hz); δ=0.88 and 0.85 ppm (together 3H, s); δ=0.78 and 0.77 ppm (together 3H, s).

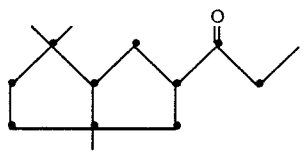

B.p.: 90° C./0.08 Torr (2 isomers).
Odor: balsamic, fruity, patchouli-like, camphor-like, woody, slightly citrus-like.

MS: m/e=208(8), 193(2), 179(27), 151(40), 139(6), 124(27), 109(39), 95(100), 81(77), 69(43), 57(61), 41(48), 29(54).

IR (film): 1710, 1455, 1410, 1385/1372/1360, 1335, 1118, 1040, 1025, 990, 985, 910, 880, 830, 795 cm⁻¹.

NMR (400 MHz, CDCl₃): main isomer: δ=2.76 ppm (1H, m); δ=2.455 ppm (2H, q, J=7 Hz); δ=1.15 ppm (3H, s); δ=1.04 ppm (3H, t, J=7 Hz); δ=0.95 ppm (3H, s); δ=0.92 ppm (3H, s).

The compounds A–E used in the following Examples are as follows:

Compound A: 1,4,4,7a-Tetramethyl-3a,4,5,7a-tetrahydro-7(6H)-ind-1-enone
Compound B: 1-Ethyl-4,4,7a-trimethyl-3a,4,5,7a-tetrahydro-7(6H)-ind-1-enone
Compound C: 3-Propionyl-1,6,6-trimethyl-bicyclo[3.3.0]-oct-2-ene
Compound D: 3-Acetyl-1,6,6,7-tetramethyl-bicyclo[3.3.0]-oct-2-ene
Compound E: 1,4,4,5,7a-Pentamethyl-3a,4,5,7a-tetrahydro-7(6H)-ind-1-enone.

EXAMPLE 6

| (a) General flowery base | |
|---|---|
| | Parts by weight |
| Terpineol | 260 |
| Hydroxycitronellal | 220 |
| Cinnamic alcohol substitute | 120 |
| Phenylethyl alcohol | 100 |
| Cinnamyl formate | 20 |
| Linalool | 15 |
| Terpenyl acetate | 10 |

(a) General flowery base

| | |
|---|---|
| Musk ketone | 10 |
| Geranyl acetate | 10 |
| Jasmin synthetic | 10 |
| Eugenol | 5 |
| Indole (10% dipropylene glycol) | 5 |
| C-10-Aldehyde (10% dipropylene glycol) | 5 |
| p-Methylacetophenone | 5 |
| Undecalactone | 5 |
| DPG | 100 |
| | 900 |

Addition of 5% of B

| | |
|---|---|
| Freshly dipped: | Intensifies broadens and harmonizes the composition, produces great freshness. |
| Bottom: | same |

Addition of 5% of C

| | |
|---|---|
| Freshly dipped: | Makes the composition richer, heavier and sweeter. |
| Bottom: | Contains the sweet character up to the end. |

Addition of 5% of D

| | |
|---|---|
| Freshly dipped: | Produces great radiance, confers a spicy-peppery note to the composition |
| Bottom: | same |

(b) Fruity base

| | Parts by weight |
|---|---|
| Methyl-phenyl-glycidic acid ethyl ester | 50 |
| Ethyl-acetyl acetate | 15 |
| Dimethyl-benzyl butyrate | 15 |
| Maltyl isobutyrate | 10 |
| Benzyl acetate | 5 |
| Ethyl acetate | 5 |
| DPG | 795 |
| | 900 |

Addition of 5% of D

| | |
|---|---|
| Freshly dipped: | Intensifies the suavity of the composition and brings about an agreeable forest scent. |

Addition of 5% of B

| | |
|---|---|
| Freshly dipped: | Confers a wonderful, sweet honey note to the composition. |

Addition of 5% of C

| | |
|---|---|
| Freshly dipped: | Confers a fresh, slightly woody (pine needle) note to the composition. |

All three produce in the bottom: fresh effect.

(c) Rose base

| | Parts by weight |
|---|---|
| Phenylethyl alcohol | 300 |
| Geraniol | 250 |
| Jasmin "lavage" | 200 |
| Citronellol | 100 |
| α-Ionone | 40 |
| C-10-Aldehyde (10% DPG) | 5 |
| C-11-Aldehyde (10% DPG) | 5 |
| | 900 |

Addition of 5% of C

| | |
|---|---|
| Freshly dipped: | Harmonizes, completes the natural rose scent. Now reminiscent of the freshly opened buds of a garden rose |
| Bottom: | Harmonizes and intensifies the bottom; homogeneous effect up to the end. |

Addition of 5% of D

| | |
|---|---|
| Freshly dipped: | See above. Reminiscent, however, of a rich red rose with the green aspect of foliage. |
| Bottom: | See above. |

(d) Fougere base

| | Parts by weight |
|---|---|
| Lavender oil French | 200 |
| Linalyl acetate | 150 |
| Tree moss | 60 |
| Coumarin | 50 |
| Patchouli oil | 30 |
| Rhodinol ex geranium oil | 30 |
| Methyl dihydrojasmonate | 30 |
| Musk ketone | 30 |
| Vetivenyl acetate | 30 |
| Geranium oil substitute | 30 |
| Amyl salicylate | 20 |
| Sandela ® | 20 |
| Linalool | 20 |
| Benzyl acetate | 15 |
| Ylang-ylang oil | 15 |
| Eugenol | 15 |
| Thyme oil | 5 |
| DPG | 50 |
| | 800 |

Addition of 5% of E

| | |
|---|---|
| Freshly dipped: | Improves the composition, rounds it off and takes away the hardness. |
| Bottom: | Makes the composition richer, finer and softer. |

Addition of 5% of B

| | |
|---|---|
| Freshly dipped: | Intensifies the herby aspect of the base. |
| Bottom: | Dry, tobacco-like effect. |

(e) Chypre base

| | Parts by weight |
|---|---|
| 1-Methylcyclododecyl methyl ether | 200 |
| Bergamot oil | 150 |
| Hydroxycitronellal | 100 |
| Pine needle oil | 80 |
| Citronellol | 80 |
| Petitgrain oil | 60 |
| Coriander oil | 40 |
| Galbanum oil | 40 |
| Cedarwood oil | 40 |
| Patchouli oil | 40 |
| Lemon oil | 40 |
| Oak moss decolorized | 20 |
| Elemi oil | 10 |
| DPG | 60 |
| | 960 |

Addition of 5% of E

| | |
|---|---|
| Freshy dippped: | Improves the fresh note of the composition and surrounds it with an agreeable coolness. |
| Bottom: | Improves the whole composition. |

Addition of 5% of A

| | |
|---|---|
| Freshly dipped: | See above. |
| Bottom: | Intensifies and improves the oak moss note of the composition. |

(f) pine base

| | Parts by weight |
|---|---|
| Rosemary essence | 200 |
| Bornyl acetate | 200 |
| Linalool | 200 |
| Terpineol | 100 |

-continued

(f) pine base

| | |
|---|---|
| Vertofix coeur | 100 |
| Galaxolid ® (50%) | 50 |
| Sapin ess. Aiguilles (needle essence) | 50 |
| Anhydrous Fir Balsam (fir resin anhydrous) | 30 |
| Eucalyptol | 25 |
| Borneol cyrst. | 10 |
| Sage oil Yugoslavian | 10 |
| C-12-Aldehyde (MNA) (10% DPG) | 5 |
| C-10-Aldehyde (10% DPG) | 5 |
| | 995 |

Addition of 5% of A

| | |
|---|---|
| Freshly dipped: | Top note fresher, stronger, more powerful and more radiant. |
| Bottom: | The fixation is clearly improved and intensified. |

Addition of 5% of E

| | |
|---|---|
| Freshly dipped: | As above. |
| Bottom: | As above. |

Addition of 5% of B, fresh: As above. Bottom: As above.

(g) Tobacco base

| | Parts by weight |
|---|---|
| α-tert-Butylcyclohexyl acetate | 400 |
| Jasmin oil synth. | 300 |
| Musk ketone | 40 |
| Sandela ® | 40 |
| Styrallyl acetate | 30 |
| Coumarin | 20 |
| Isobutylquinoline (10% DPG) | 10 |
| Lavender oil | 10 |
| Vetiver oil | 10 |
| Galbanum oil | 10 |
| Vassura oil | 10 |
| DPG | 40 |
| | 920 |

Addition of 5% of A

| | |
|---|---|
| Freshly dipped: | Intensifies and rounds off the flowery note, confers great radiance to the composition. becomes fresher. |
| Bottom: | More powerful. |

Addition of 5% of E

| | |
|---|---|
| Freshly dipped: | Enriches the herby-woody note of the composition. |
| Bottom: | As above. |

Addition of 5% of B

| | |
|---|---|
| Freshly dipped: | Harmonizing effect on the composition base. |
| Bottom: | As above. |

(h) Tobacco flavour

| | Parts by weight | |
|---|---|---|
| Thibetolide ™ (Givaudan) (pentadecanolide) | 4 | 4 |
| Sandalwood oil | 15 | 15 |
| Cedryl acetate | 15 | 15 |
| α-Ionone | 1 | 1 |
| β-Ionone | 5 | 5 |
| Keto-isophorone | 20 | 15 |
| β-Caryophyllene | 5 | 5 |
| Geranyl acetate | 5 | 5 |
| Propylene glycol | 400 | 400 |
| Alcohol 96% | 530 | 530 |
| A | — | 5 |
| | 1,000 | 1,000 |

By the addition of A the originally present, sweetish, woody note is clearly reduced in the above composition. Upon smoking the flavored tobacco there is prominent an agreeable tobacco-like, tarry/woody note which is reminiscent of Virginia tobacco.

I claim:

1. A compound of the formula

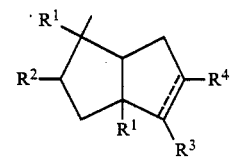

wherein:
R¹ represents methyl or ethyl,
R² represents hydrogen or methyl,
the dotted line represents an optional carbon-carbon bond,
R³ is hydrogen and R⁴ represents acetyl or propionyl.

2. A compound according to claim 1 which is 3-acetyl-1,6,6-trimethyl-bicyclo-[3.3.0]-oct-2-ene.

3. A compound according to claim 1 which is 3-acetyl-1,6,6,7-tetramethyl-bicyclo-[3.3.0]-oct-2-ene.

4. A compound according to claim 1 which is 3-propionyl-1,6,6-trimethyl-bicyclo-[3.3.0]-oct-2-ene.

5. A compound of the formula

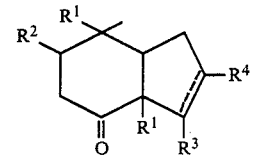

wherein:
R¹ represents methyl or ethyl,
R² represents hydrogen or methyl,
the dotted line represents an optional carbon-carbon bond,
R³ represents methyl or ethyl, and,
R⁴ represents hydrogen or methyl,
with the exception of 1,4,4,7a-tetramethyl-3a,4,5,7a-tetrahydro-7(6H)-ind-1-enone.

6. A compound according to claim 5 which is 1,4,4,5,7a-pentamethyl-3a,4,5,7a-tetrahydro-7(6H)-ind-1-enone.

7. A compound according to claim 5 which is 1-ethyl-4,4,7a-trimethyl-3a,4,5,7a-tetrahydro-7(6H)-ind-1-enone.

8. A compound according to claim 5 which is 1,2,4,4,7a-pentamethyl-3a,4,5,7a-tetrahydro-7(6H)-ind-1-enone.

* * * * *